(12) United States Patent
Jiang et al.

(10) Patent No.: US 7,672,058 B2
(45) Date of Patent: Mar. 2, 2010

(54) COMPOUND EYE

(75) Inventors: Hongrui Jiang, Madison, WI (US);
Liang Dong, Ames, IA (US)

(73) Assignee: Wisconsin Alumni Research Foundation, Madison, WI (US)

(*) Notice: Subject to any disclaimer, the term of this patent is extended or adjusted under 35 U.S.C. 154(b) by 99 days.

(21) Appl. No.: 11/856,384

(22) Filed: Sep. 17, 2007

(65) Prior Publication Data

US 2009/0073569 A1 Mar. 19, 2009

(51) Int. Cl.
*G02B 27/10* (2006.01)
(52) U.S. Cl. .................. 359/665; 359/626; 359/666
(58) Field of Classification Search ......... 359/619–626, 359/665–667, 656; 362/258; 250/239, 208.1
See application file for complete search history.

(56) References Cited

U.S. PATENT DOCUMENTS

| | | | |
|---|---|---|---|
| 6,369,954 B1 | 4/2002 | Berge et al. | |
| 7,068,439 B2 | 6/2006 | Esch et al. | |
| 7,085,065 B2 | 8/2006 | Silver | |
| 7,106,519 B2* | 9/2006 | Aizenberg et al. | 359/620 |
| 7,359,124 B1 | 4/2008 | Fang et al. | |
| 7,382,544 B2 | 6/2008 | Cernasov | |
| 2007/0109438 A1* | 5/2007 | Duparre et al. | 348/335 |
| 2007/0177276 A1 | 8/2007 | D'ardhuy et al. | |
| 2007/0211207 A1 | 9/2007 | Lo et al. | |
| 2007/0279758 A1* | 12/2007 | Jiang et al. | 359/666 |

OTHER PUBLICATIONS

Article from Nature Publishing Group, vol. 425, dated Sep. 2003, pp. 383-385, entitled "Video-speed electronic paper based on electrowetting," by Robert A. Hayes and B.J. Feenstra.
Article from Economist.com, Science Technology Quarterly, dated Jun. 10, 2004, pp. 1-4, entitled "Materials: Smart-fluid technology is moving from laboratory curiosity to commercial possibility, and is being put to use in cars, bridges and even digital cameras."
Ki-Hun Jeong, "Biologically Inspired Artificial Compound Eyes," Science, vol. 312, dated Apr. 28, 2006, pp. 557-561.

* cited by examiner

*Primary Examiner*—Ricky L Mack
*Assistant Examiner*—Vipin M Patel
(74) *Attorney, Agent, or Firm*—Boyle Fredrickson, S.C.

(57) ABSTRACT

A compound eye is provided. The compound eye includes a microfluidic device defining a plurality of wells therein. A plurality of lenses are disposed in corresponding wells of the microfluidic device. Each lens has a tunable focal length. A tuning structure tunes the focal length of each lens in response to a predetermined stimulus.

16 Claims, 10 Drawing Sheets

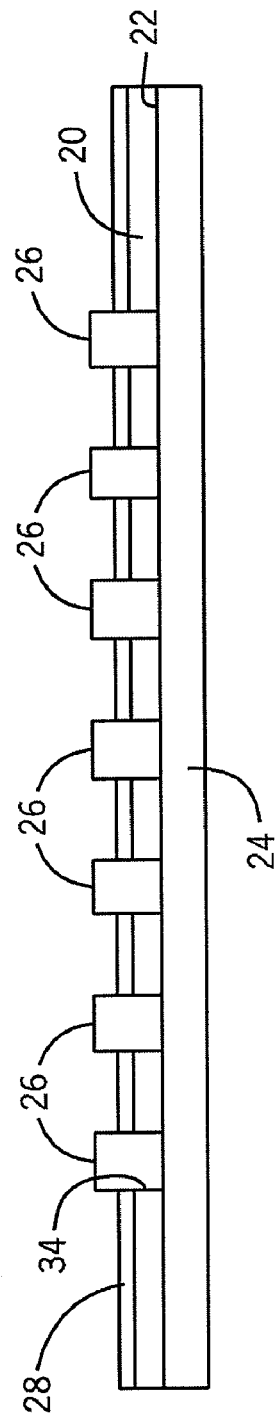

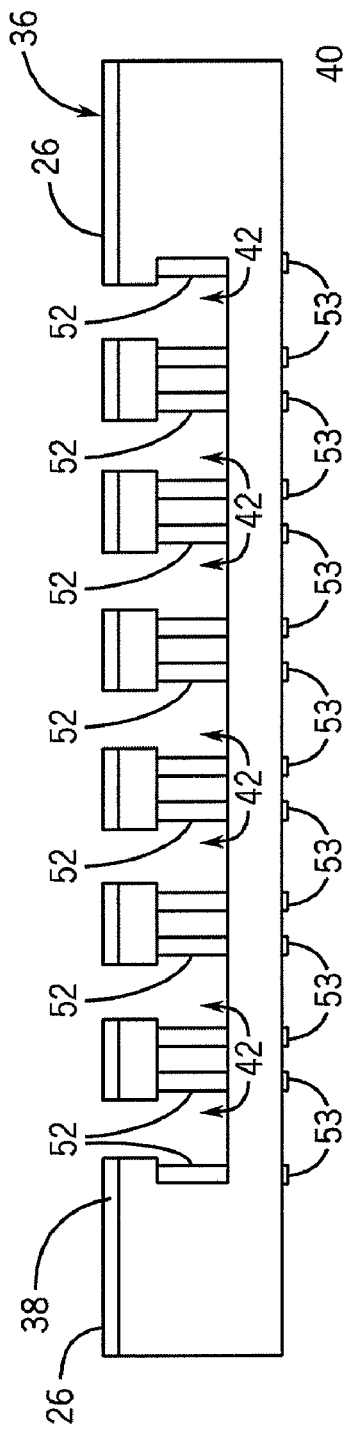
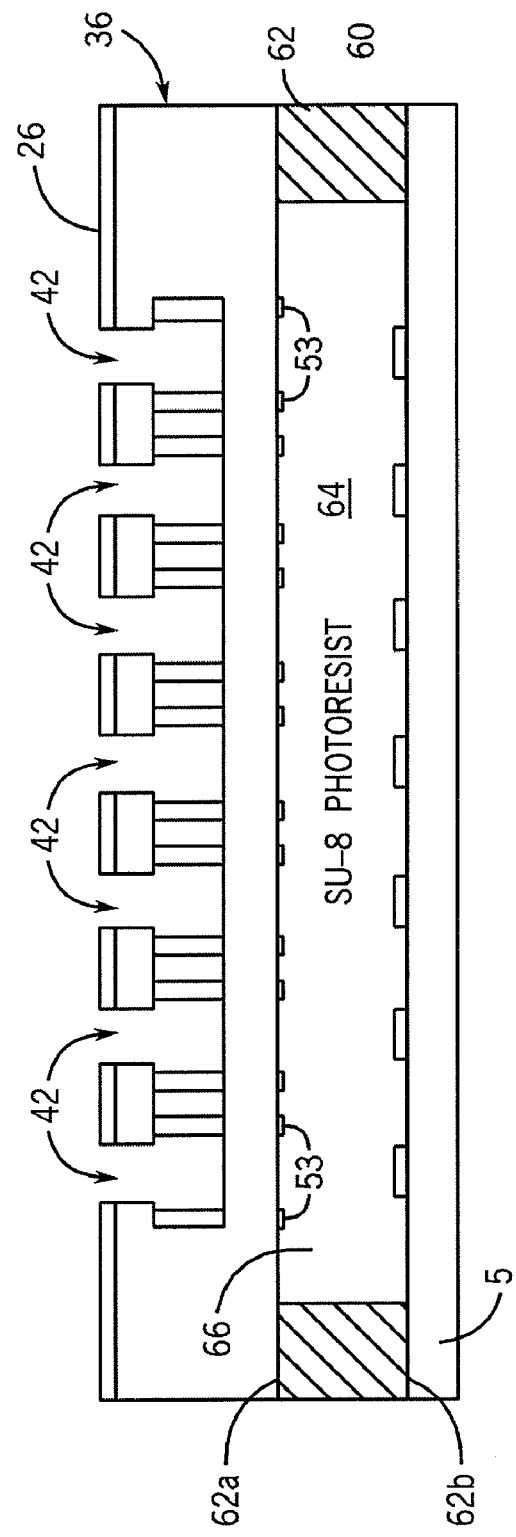
FIG. 6
FIG. 7

COMPOUND EYE

REFERENCE TO GOVERNMENT GRANT

This invention was made with United States government support awarded by the following agencies: N-00014-04-1-0659. The United States government has certain rights in this invention.

FIELD OF THE INVENTION

This invention relates generally to microfluidic devices, and in particular, to an artificial compound eye incorporating a plurality of variable focus, optical microlenses that are autonomously tuned by local environmental parameters.

BACKGROUND AND SUMMARY OF THE INVENTION

Optical imaging and microscopy are extremely important in biological studies and biomedical applications. As such, there has been a significant amount of research dedicated to the creation of optical components and modules at the microscale. This research has led to the development of such products as semiconductor-based avalanche photo-detector (APD) that can detect single photons and artificial retinas. However, compared to the maturity and tremendous success of other miniaturized systems such as integrated circuits and image processing systems, the development in miniaturized optical systems as a whole lags behind. For example, current microscopic optical systems are generally bulky and expensive. Consequently, there exists an ongoing need for optical imaging and microscopy systems that are much smaller scale and less expensive than present systems.

Traditional man-made optical systems are comprised of multiple lenses wherein one or more of the lenses are physically displaced to realize variable-focus. Traditional lens systems realize tuning of the focal length by mechanical displacement of fixed-focal lenses, thereby requiring complicated mechanical components and controlling systems. Tunable microlenses adjust the focal lengths of the lenses by changing either the shapes of the microlenses or the refractive indices of the lens materials. Different mechanisms have been used in these prior tunable microlenses, including reorientation and redistribution of liquid crystals, electrowetting of a liquid droplet, electrochemically activating liquids, and mechanical actuation of polymeric materials or liquids. While these microlens technologies do simplify lens tuning, they still require complicated electronic and mechanical control systems that do not readily scale down to the microscale level and that consume too much power. Alternatively, tunable microlenses have been fabricated from responsive gel microparticles. These types of microlenses take advantage of the change in refractive indices of gels due to reactions to proteins or responses to temperature. However, as a microlens for optical applications, these types of microlenses fabricated from responsive gel microparticles have their drawbacks, such as a small focal length tuning range, difficulty in accurate controlling the shape of the lens, low transparency to visible light and a rough lens surface.

Natural eyes generally fall into two categories, namely, camera-eyes and compound eyes. A camera-eye (e.g., a human eye) generally relies on a single-aperture lens to focus images onto a retina. In the human eye, focusing at different distances is made possible by altering the tension on the flexible crystalline lens, and thus the curvature and focal length of the lens, by ciliary muscles. Compared to compound eyes, camera-eyes have high sensitivity and resolution but small field of view (FOV). Because of the limited viewing angle, the head and/or body must move or rotate to capture the complete visual image of the surrounding area. Therefore, mimicking this type of eye generally requires extensive and complicated electronic and mechanical control systems that, as heretofore described, does not readily scale down to the microscale and consumes a significant amount of power. Furthermore, owing to diffraction effects, a simple scaling down of known classical image optics based on camera-eyes would drastically reduce the resolution and potentially also the sensitivity.

On the other hand, for small invertebrates with external skeletons, such as flies and moths, utilize compound eyes. Compound eyes combine small eye volumes with a large field of vision at the cost of comparatively low spatial resolution due to the small image field of each eye. These compound eyes provide sufficient visual information without overloading their owners' brains with complicated image processing. Similar to manmade microlens arrays, compound eyes utilize multiple lens elements. However, achieving a wide field of vision in microlens arrays has been hindered by the inherent flatness of the arrayed optical components fabricated using semiconductor technologies. In addition, the need to align multiple layers of arrayed components during assembly is a big disadvantage compared to forming an optical system using single lenses.

Therefore, it is a primary object and feature of the present invention to provide an artificial compound eye incorporating a plurality of variable focus, optical microlenses that are autonomously tuned by local environmental parameters.

It is a further object and feature of the present invention to provide an artificial compound eye incorporating a plurality of variable focus, optical microlenses that is much smaller in scale and less expensive than present lenses.

It is a still further object and feature of the present invention to provide an artificial compound eye incorporating a plurality of variable focus, optical microlenses that is compact and easily fabricated.

In accordance with the present invention, an artificial compound eye is provided. The compound eye includes a base having a plurality of wells formed therein. A plurality of tunable ommatidia having focal lengths are received in corresponding wells.

The compound eye may also include a plurality of actuators. Each actuator is engageable with a corresponding ommatidium for tuning the focal length of the ommatidium. Each actuator includes a hydrogel. The hydrogel has a configuration responsive to a predetermined stimulus. The hydrogel is movable between a first configuration wherein the lens has a first focal length and a second configuration wherein the lens has a second focal length in response to a predetermined stimulus. It is contemplated for the predetermined stimulus to be temperature.

The compound eye may include a plurality of photodetectors. Each photodetector detects an image received by a corresponding ommatidium. A plurality of waveguides guide the image from corresponding ommatidia to corresponding photodetectors.

The base of the compound eye may include a slip having first and second sides and a plurality of apertures therethrough. Each aperture communicates with a corresponding well. Each ommatidium includes first and second layers having an interface. The interface has an outer periphery. The first layer is formed from an oil-based fluid and the second layer is formed from a water-based fluid. At least of a portion of the second layer of each ommatidium is received in a corresponding well.

The base of the compound eye includes an outer surface having the plurality of wells formed therein and an inner surface. It is contemplated for the outer surface of the base to be generally arcuate. A cover may overlap the outer surface of the base. A heating element may be positioned adjacent the inner surface of the base.

In accordance with a further aspect of the present invention, an artificial compound eye is provided. The compound eye includes a microfluidic device defining a plurality of wells therein. A plurality of lenses are disposed in corresponding wells of the microfluidic device. Each lens has a tunable focal length. A tuning structure is provided for tuning the focal length of each lens in response to a predetermined stimulus.

The tuning structure includes a plurality of hydrogels engageable with corresponding lenses. Each hydrogel is movable between a first configuration wherein the corresponding lens has a first focal length and a second configuration wherein the corresponding lens has a second focal length in response to a predetermined stimulus. It is contemplated for the predetermined stimulus to be temperature.

The compound eye may include a plurality of photodetectors. Each photodetector detects an image received by a corresponding lens. A plurality of waveguides guide the image from corresponding lenses to corresponding photodetectors.

The microfluidic device includes a slip having a plurality of apertures therethrough. Each aperture communicates with a corresponding well. Each lens includes first and second layers having an interface. The interface has an outer periphery. The first layer is formed from an oil-based fluid and the second layer is formed from a water-based fluid. At least of a portion of the second layer of each lens is received in a corresponding well.

The base of the compound eye includes an outer surface having the plurality of wells formed therein and an inner surface. It is contemplated for the outer surface of the base is generally arcuate. A cover may overlap the outer surface of the base. A heating element may be positioned adjacent the inner surface of the base.

In accordance with a still further aspect of the present invention, a compound eye is provided. The compound eye includes a microfluidic device with a base having an outer surface defining a plurality of wells and an inner surface. A first fluid is disposed in the plurality of wells. A second fluid intersects the first fluid at a plurality of interfaces. Each interface defines a lens having a focal length. A tuning structure tunes the focal length of each lens in response to a predetermined stimulus.

The tuning structure includes a plurality of hydrogels positioned in corresponding wells. Each hydrogel is movable between a first configuration wherein the corresponding lens has a first focal length and a second configuration wherein the corresponding lens has a second focal length in response to a predetermined stimulus. A plurality of photodetectors detect images received by corresponding lenses. A plurality of waveguides guide the images from corresponding lenses to corresponding photodetectors.

The microfluidic device includes a slip affixed to the outer surface and having a plurality of apertures therethrough. Each aperture communicates with a corresponding well. The first fluid is a water-based fluid and the second fluid is an oil-based fluid. The outer surface of the base is generally arcuate. The microfluidic device may also include a cover overlapping the outer surface of the base and a heating element adjacent the inner surface of the base.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 2 is a cross-sectional view showing a first step in the fabrication of a compound eye of FIG. 1;

FIG. 3 is a cross-sectional view showing a second step in the fabrication of a compound eye of FIG. 1;

FIG. 6 is a cross-sectional view of a fifth step in the fabrication of a compound eye of FIG. 1;

FIG. 7 is a cross-sectional view of a sixth step in the fabrication of a compound eye of FIG. 1;

DETAILED DESCRIPTION OF THE DRAWINGS

Figure 1:
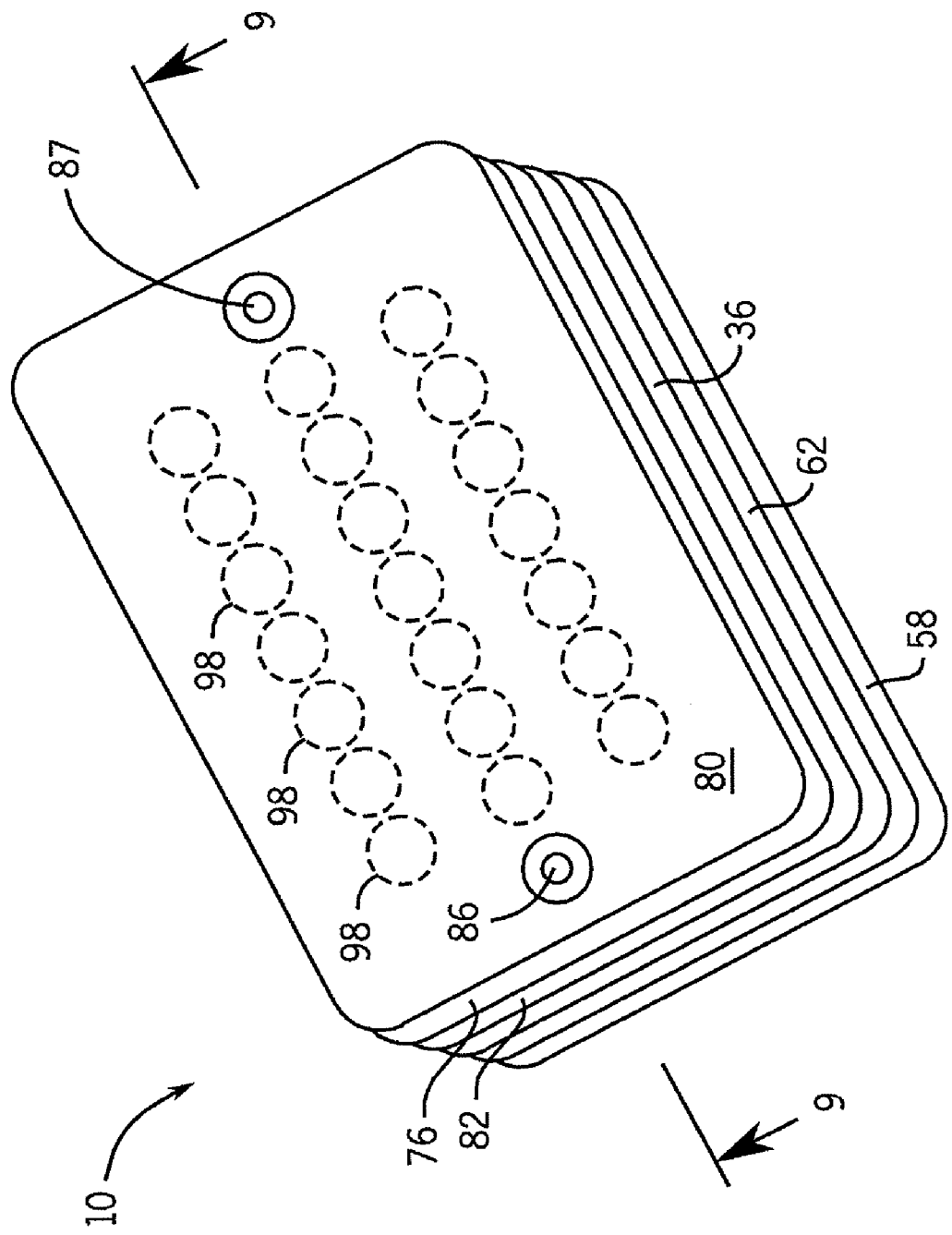
FIG. 1 is an isometric view of a compound eye in accordance with the present invention.
Figure 4:
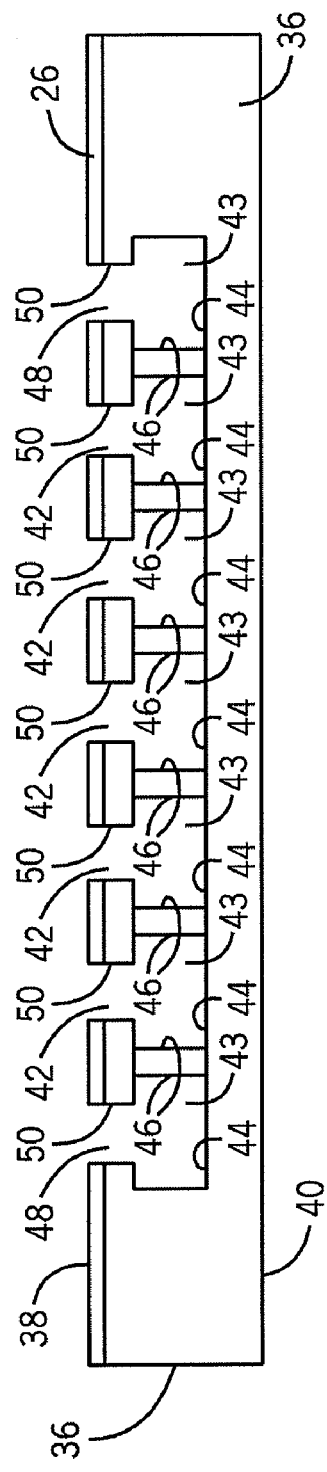
FIG. 4 is a cross-sectional view showing a third step in the fabrication of a compound eye of FIG. 1.
Figure 8:
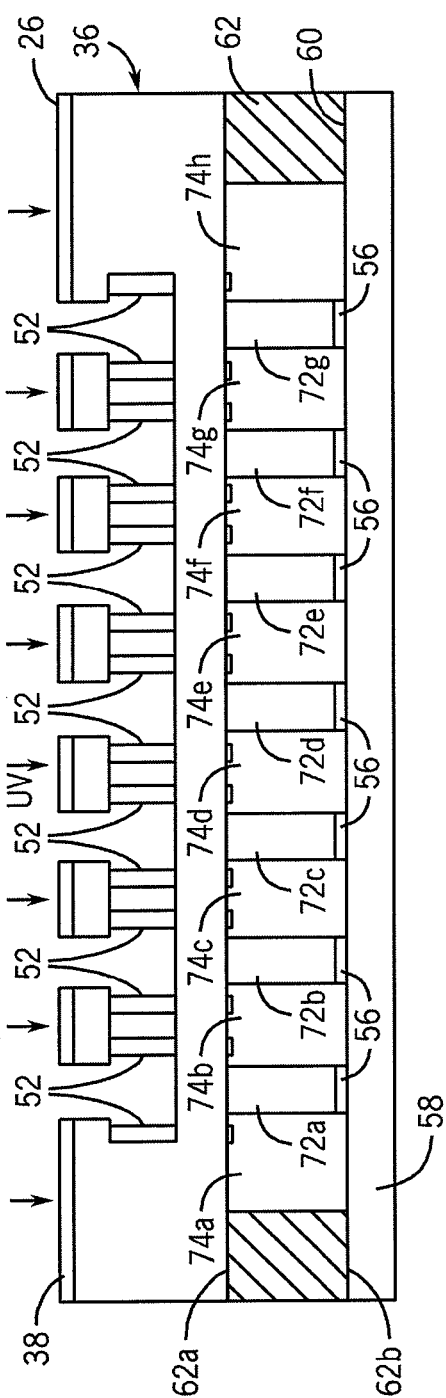
FIG. 8 is a cross-sectional view of a seventh in the fabrication of a compound eye of FIG. 1.
Figure 9:
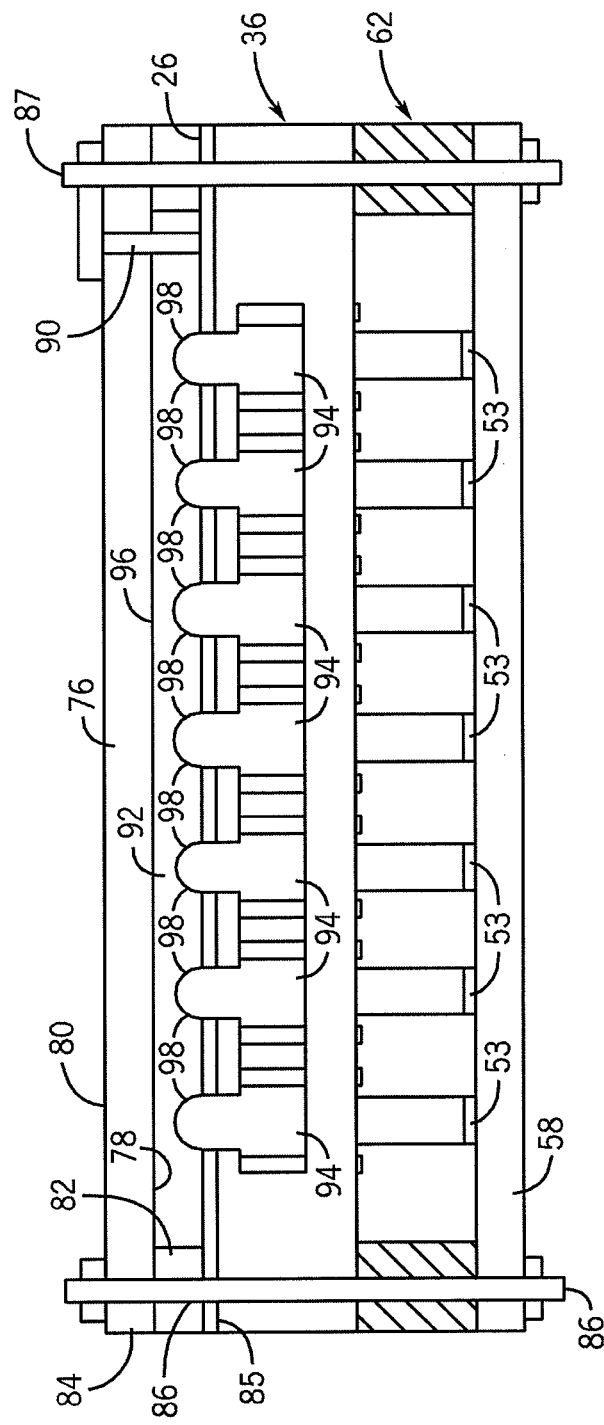
FIG. 9 is a cross-sectional view of a compound eye of the present invention taken along line 9-9 of FIG. 1.

Referring to FIGS. 1 and 9, a first embodiment of a compound eye in accordance with the present invention is generally designated by reference numeral 10. Referring to FIGS. 2-8, in order to fabricate compound eye 10, a replica molding process is used. More specifically, a cartridge (not shown) is deposited on upper surface 14 of first glass substrate 12. First well mold 16 fabricated from a photosensitive polymer resin, such as SU-8 photoresist, is also positioned on upper surface 14 of first glass substrate 12 within the cartridge. A liquid photopolymer, e.g, poly(dimethylsiloxane) (PDMS), is poured into the cartridge and thermally cured to form first base portion 18. Thereafter, first base portion 18 is released from first well mold 16 and the cartridge.

Second base portion 20 is formed by positioning a second cartridge (not shown) on upper surface 22 of second glass substrate 24. Second well mold 26 fabricated from a photosensitive polymer resin, such as SU-8 photoresist, is also positioned on upper surface 22 of glass substrate 24 within the cartridge. A liquid photopolymer, e.g, PDMS, is poured into the cartridge and thermally cured to form second base portion 20. Once second base portion 20 is cured, film 26 is sputtered on upper surface 28 of second base portion 20. Film 26 may be fabricated from gold or other suitable material and is rendered hydrophobic with alkanethiols, for reasons hereinafter described. Thereafter, second base portion 20 is released from second well mold 26 and the cartridge.

Once first and second base portions 18 and 20, respectively, are released from their corresponding molds, second base portion 20 is deposited on upper surface 32 of first base portion 18 such that passageways 34 through second base portion 18 are axially aligned with depressions 36 in upper surface 32 of first base portion 18 and such that the outer periphery of second base portion 20 is aligned with the outer periphery of first base portion 18. First and second base portions 18 and 20, respectively, are permanently bonded together after an oxygen plasma surface treatment in a reactive ion etching system, FIG. 4. Once assembled, first and second base portions 18 and 20, respectively, define base 36. Base 36 includes upper and lower surfaces 38 and 40, respectively. A plurality of wells 42 extend into upper surface 38 of base 36. Each well 42 includes a lower portion 43 defined by closed bottom wall 44 and sidewall 46 extending therefrom. Each well 42 further includes a reduced diameter portion 50 defining aperture 48. Each aperture 48 communicates with film 26 sputtered on upper surface 38 of base 36 and with lower portion 43 of a corresponding well 42. It is noted that the oxygen plasma treatment, heretofore described, renders the PDMS surfaces of base 36, including sidewalls 46 of wells 42, hydrophilic.

Figure 5:
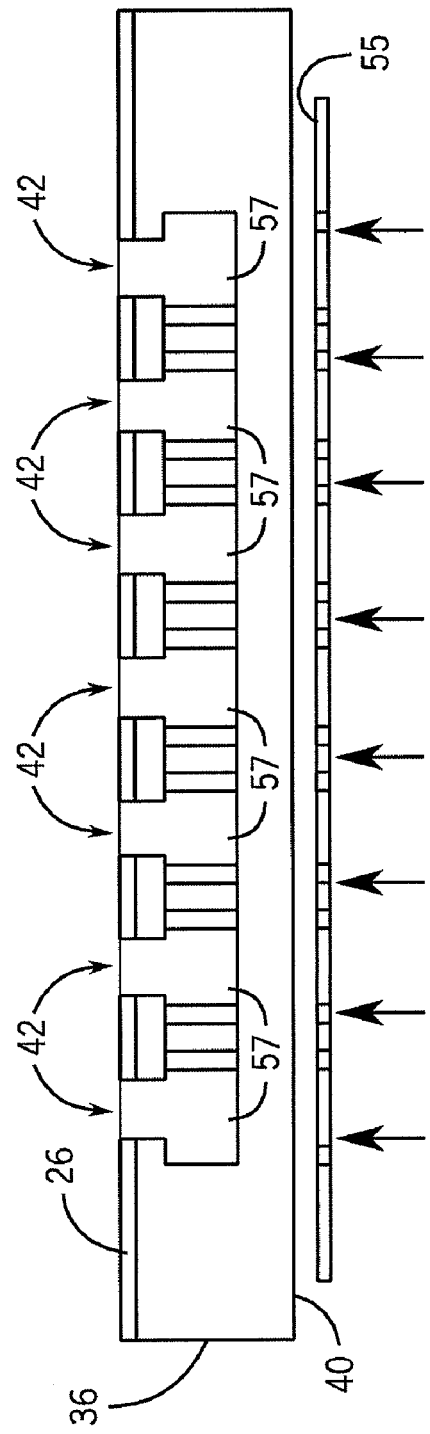
FIG. 5 is a cross-sectional view showing a fourth step in the fabrication of a compound eye of FIG. 1.

Referring to FIGS. 5-6, stimuli-responsive hydrogel microposts 52 are patterned sidewalls 46 of wells 42 by exposure to ultraviolet light that passes through a photomask film 55 and lower surface 40 of base 36. The unpolymerized portions of the hydrogel 57 are washed away from wells 42 with ethanol. In applications wherein hydrogel microposts 52 are thermally responsive, a plurality of ring-shaped microheaters 53 may be used individually control the local temperature of the hydrogel microposts 52. The plurality of ring-shaped microheaters 53 are attached to lower surface 40 of base 36 in axial alignment with the corresponding hydrogel microposts 52, FIG. 6. Microheaters 53 are wired to an external controller[s] (not shown) which, in turn, control activation of the microheaters 53.

A self-alignment technique is applied to fabricate optical waveguides in axial alignment with wells 42 in base 36, FIGS. 7-8. More specifically, an array of photodetectors 56 is mounted onto substrate 58 (e.g., a printed circuit board). Lower surface 40 of base 36 is separated a predetermined distance from upper surface of 60 of substrate 58 by gasket 62. Gasket 62 includes an upper surface 62a engaging lower surface 40 of base 36 and a lower surface 62b engaging upper surface 60 of substrate 58 so as to form chamber 64 therebetween. A photosensitive polymer resin 66, such as SU-8 photoresist, is flowed into chamber 64. Ultraviolet light is directed toward upper surface 38 of base 36. It can be appreciated that film 26 blocks a first portion of the ultraviolet light directed at upper surface 38 of base 36. However a second portion of the ultraviolet light passes through wells 42 in base 36 so as to polymerize a plurality of portions 72a-72g of resin 66 in chamber 64. The portions 72a-72g of resin 66 exposed to the ultraviolet light experience polymeric cross linking, causing an increase in their chemical resistance and refractive index, compared to the unexposed portion of 74a-74h of resin 66. The difference in the refractive indices between the portions 72a-72g of resin 66 exposed to the ultraviolet light and then non-exposed portions of 74a-74h of resin 66 brings about polymer waveguides that are self-aligned with wells 42 in base 36.

Mircofluidic device 10 further includes oil container 76 having an inner surface 78 and an outer surface 80, FIG. 9. It is contemplated to fabricate oil container 76 from PDMS or other suitable material. Spacer 82 is position adjacent outer periphery 84 of oil container 76 and includes upper surface 86 in engagement with inner surface 78 of oil container 76 and a lower surface 85 engaging film 26. First and second clamping bars 86 and 87 extends though oil container 76, spacer 82 base 36, gasket 62 and substrate 58. Clamping elements 88 and 90 are positioned on opposite ends of clamping rods 86 and 87 so as to compress microfluidic device 10 such that spacer 82 provides a fluid-tight connection between oil container 76 and film 26. As best seen in FIG. 9, once assembled, inner surface 78 of oil container 76 and film 26 define oil receiving chamber 92 therebetween.

In order to form the liquid microlenses of the compound eye of the present invention, water droplets 94 are loaded into wells 42 of base 36 through filling hole 90 in oil container 76. Thereafter, oil receiving chamber 92 of oil container 76 is filled with a suitable oil 96, e.g., mineral oil, and filling hole 90 is sealed in any suitable matter. The intersection of the hydrophobic film 26 and the hydrophilic reduced diameter portion 50 of wells 42 defined contact lines that pin water droplets 94 at the upper edges of apertures 48 so as to form a plurality of liquid menisci 98 at the water-oil interfaces. As hereinafter described, when hydrogel microposts 52 are exposed to a predetermined stimulus, e.g., temperature, light, etc., microposts 52 expand and shrink by absorbing and releasing water via the hydrogel network interstitials. This, in turn, results in a volume change in the water received in wells 42. The net physical volume changes in both hydrogel microposts 52 and the water received in wells 42 cause changes in the pressure differences across the water-oil interface (P) which, in turn, directly determines the outcome of the liquid menisci 98. The stationary pinned contact lines translate changes in the water volumes into changes in the contact angles of the liquid meniscuses ($\theta$), and thus, the focal lengthes of the microlenses $\theta$ may attain any value in the interval $-(90°-\theta_\beta) \leq \theta \leq \theta_\alpha$ by varying P, where $\theta_\alpha$ and $\theta\beta$ are the water contact angles on the hydrophobic surface of film 26 and hydrophilic sidewalls 46 of wells 42, respectively.

As heretofore described, it is contemplated to fabricate hydrogel microposts 52 from a NIPAAm hydrogel that expands at low temperatures and contracts at high temperatures with a volume transition temperature of approximately 50° C. The temperature of the hydrogel microposts 52 may be controlled by microheaters 53. Here, the expansion and contraction of hydrogel microposts 52 only occurs within wells 42 due to the physical restraint of sidewalls 46 of wells 42. At low temperatures, the liquid menisci 98 grow because the added physical volumes of hydrogel microposts 52 are larger than the volumes of the water in wells 42 lost to absorption by hydrogel microposts 52. At high temperatures, liquid menisci 98 retreat because the water released from physical shrinking of hydrogel microposts 52 is unable to compensate for the decrease in physical volumes of hydrogel microposts 52. More specifically, as the temperatures increase, the microlenses become more convergent. As a result, the focal lengths of the microlenses are tuned from infinity to several millimetres, thus allowing the microlenses to zoom in on a target area.

Alternatively, the liquid microlenses may be responsive, either entirely or partially, to light. More specifically, hydrogel microposts 52 may be fabricated from a light-responsive hydrogel that responds to the wavelength of the light incident onto them and contract accordingly, pulling down the oil-water interface towards the water and eventually into the water, rendering a more convergent lens. When light is off, the hydrogel microposts 52 expand back, pushing the oil-water interface back towards the oil, thus restoring a more divergent lens. Once again, to pin the oil-water interfaces at the edges of the apertures 48 of wells 42, reduced diameter portions 50 of wells are treated to be hydrophilic and film 26 on upper surface 38 of base 36 is treated to be hydrophobic. Therefore, hydrophobic-hydrophilic contact lines are formed and will pin the oil-water interfaces via surface tension. In this embodiment, the volumes of hydrogel microposts 52 are defined through ultraviolet (UV) exposure.

The aforementioned liquid microlenses can smartly focus on objects at different distances. By causing the hydrogel microposts 52 to change their volumes, the microlenses autonomously tunes to focus on desired targets. Due to a hydrogel's ability to convert chemical energy to mechanical energy, the hydrogel microposts 52 simultaneously exhibit both sensing and actuating functions to respond to local environments.

Referring to FIGS. 10-13, an alternate embodiment of a compound eye in accordance with the present invention is generally designated by reference numeral 100. Compound eye 100 includes base 36 as heretofore described, having film 26 sputtered on upper surface 38 thereof, stimuli-responsive hydrogel microposts 52 patterned on sidewalls 46 of wells 42; and in applications wherein hydrogel microposts 52 are thermally responsive, a plurality of ring-shaped microheaters 53 attached to lower surface 40 of base 36 in axial alignment with the corresponding hydrogel microposts 52. Microheaters 53 are wired to an external controller[s] (not shown) which, in turn, control activation of the microheaters 53.

Figure 10:
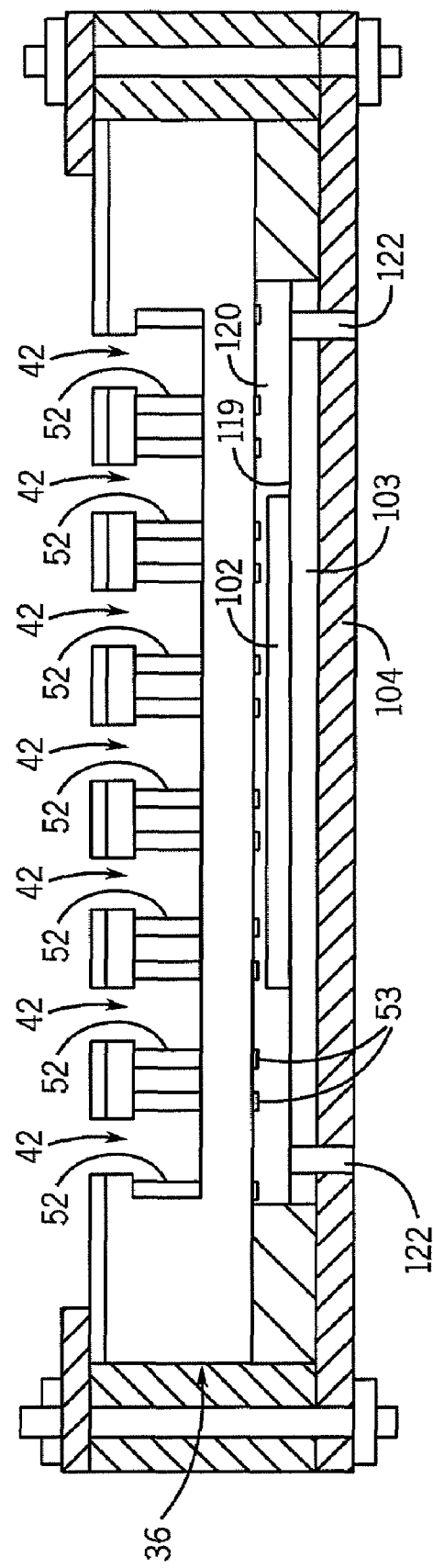
FIG. 10 is a cross-sectional view showing a first step in the fabrication of an alternative embodiment of a compound eye in accordance with the present invention.
Figure 11:
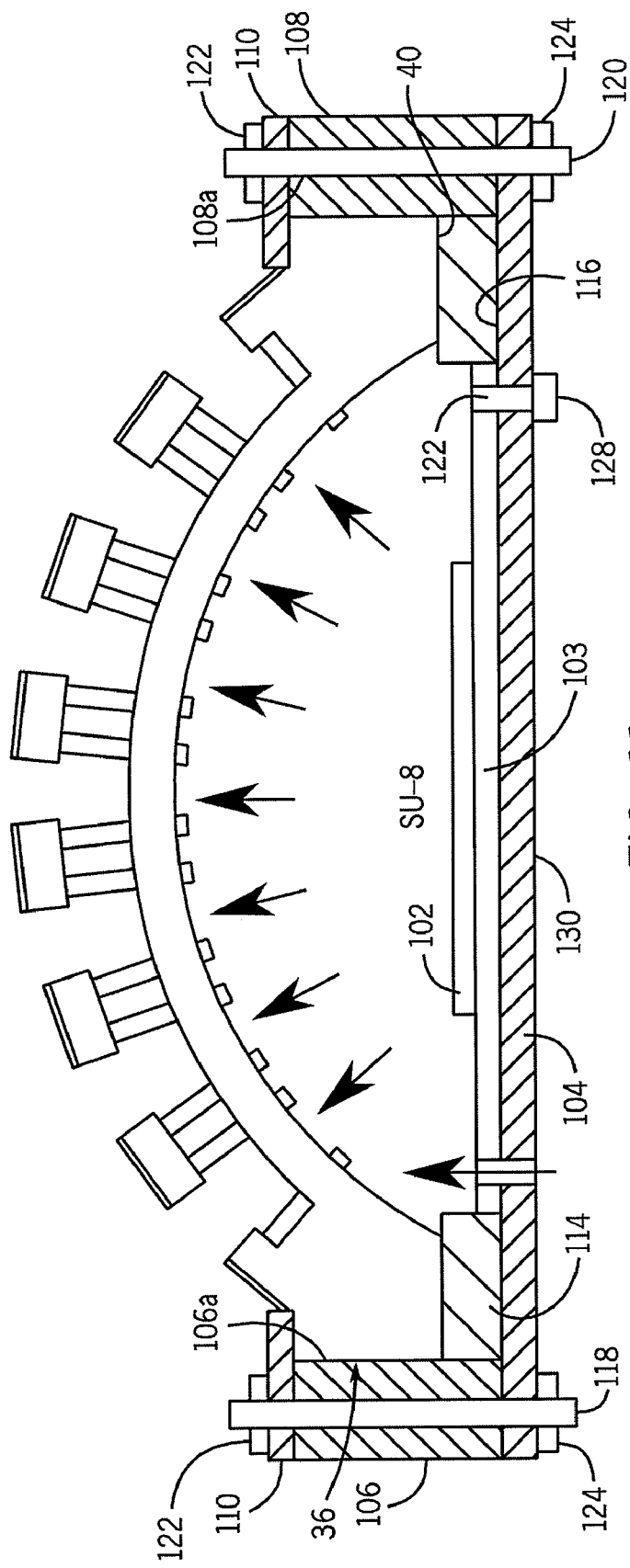
FIG. 11 is a cross-sectional view showing a second step in the fabrication of the compound eye of FIG. 10.

Array of photodetectors 102 is mounted onto upper substrate 103 (e.g., a printed circuit board) which in turn is supported on lower substrate 104. Spacers 106 and 108 are positioned between substrate 104 and corresponding dampers 110 at a location adjacent the outer periphery of base 36. In addition, gasket 114 is positioned between upper surface 116 of substrate 104 and lower surface 40 of base 36 abutting inner surfaces 106a and 108a of spacers 106 and 108, respectively. First and second clamping bars 118 and 120, respectively, extend though corresponding dampers 110; spacers 106 and 108, respectively; and substrate 104. Clamping elements 122 and 124 are positioned on opposite ends of clamping rods 118 and 120 so as to compress compound eye 10 such that gasket 114 provides a fluid-tight seal between lower surface 40 of base 36 and upper surface 116 of substrate 104 along the outer periphery thereof. As best seen in FIG. 10, once assembled, lower surface 40 of base 36 and upper surface 119 of upper substrate 103 define thin chamber 120 therebetween.

A photosensitive polymer resin 124, such as SU-8 photoresist, is flowed into chamber 120 though one or more filling holes 122 in substrates 103 and 104. Resin 124 is dispensed into chamber 124 under pressure such that base 36 is deformed by pressure and becomes a spherical dome, FIG. 11. The desired shape of the dome is reached by dispensing a desired amount of resin 124 in chamber 120. Thereafter, filling holes 122 are sealed in any conventional manner, such as by caps 128 fixed to lower surface 130 of substrate 104.

Figure 12:
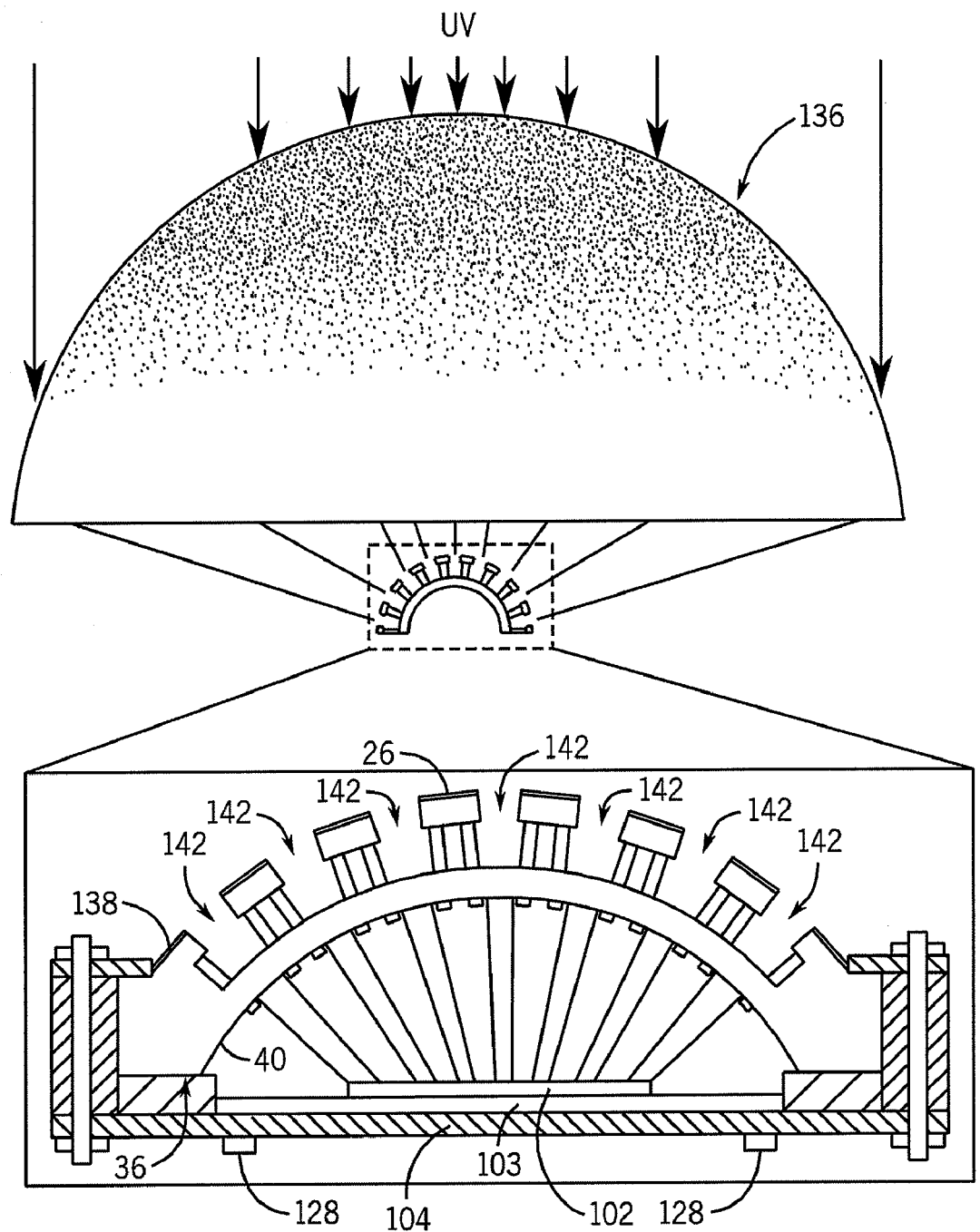
FIG. 12 is an exploded view, partially in section, showing a third step in the fabrication of the compound eye of FIG. 10.
Figure 13:
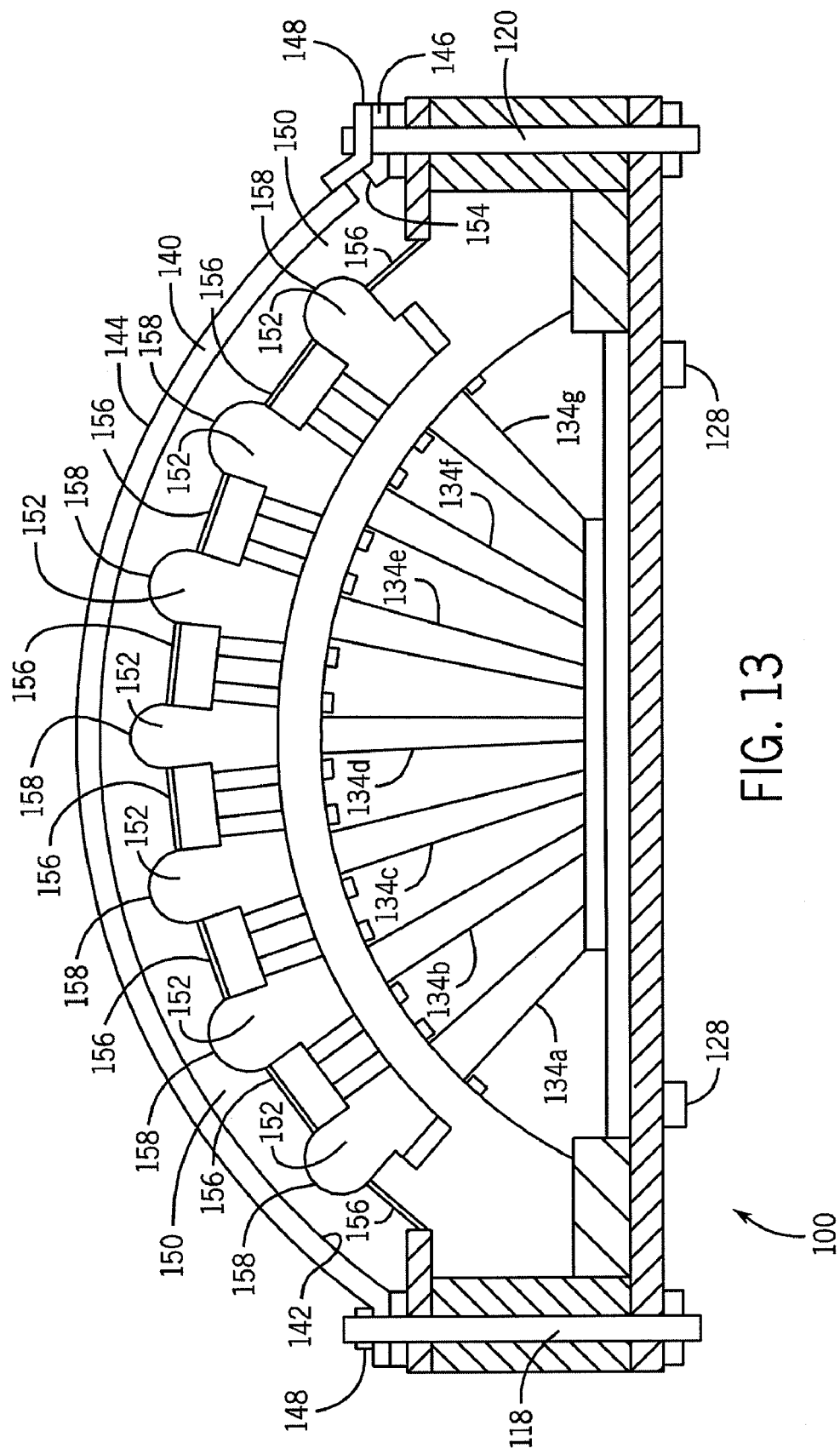
FIG. 13 is a cross-sectional view of the compound eye of FIG. 10.
Figure 14:
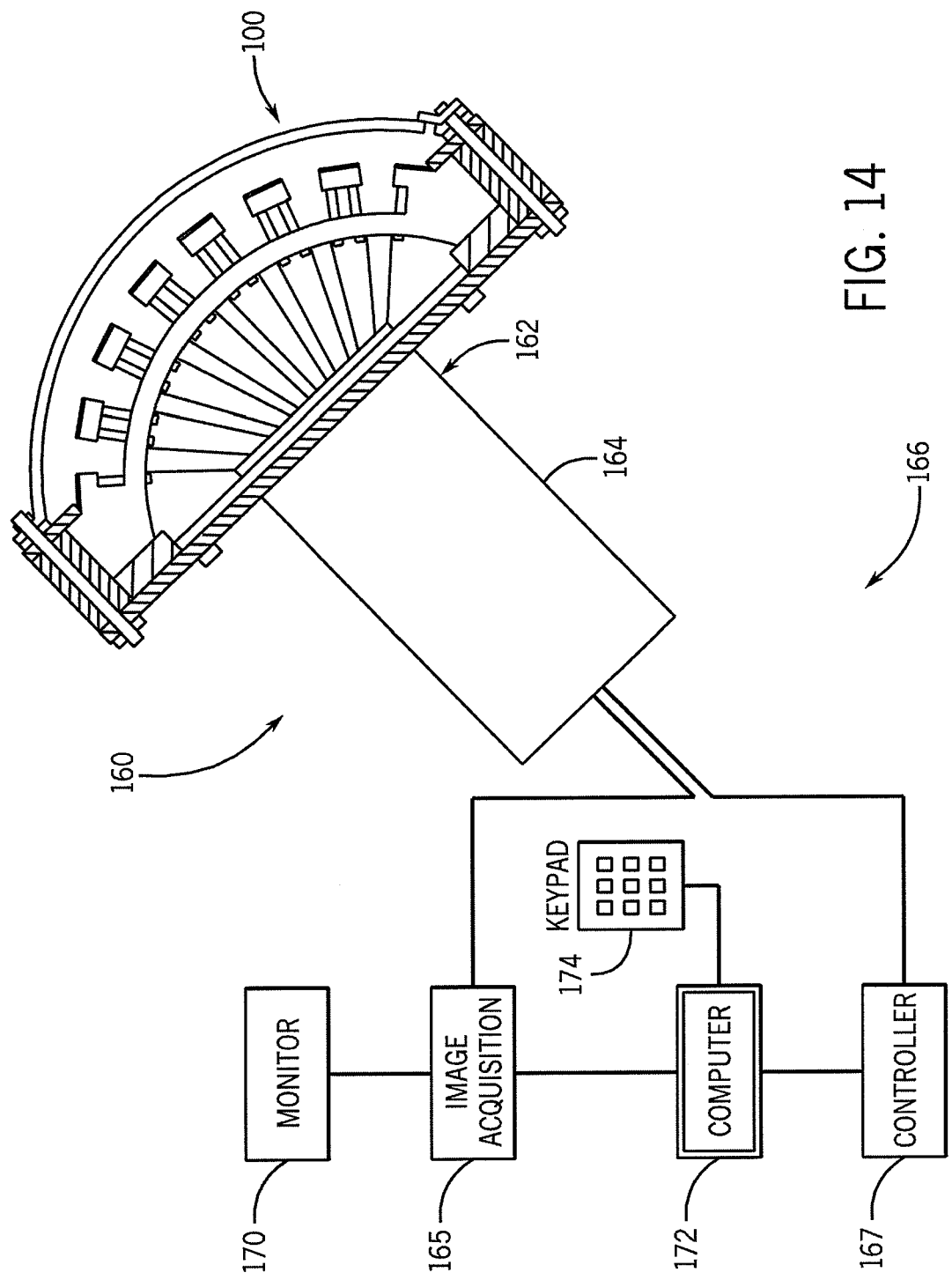
FIG. 14 is a schematic view of a laparoscope incorporating a compound eye in accordance with the present invention.

To form self-aligned waveguides 134a-134g, FIGS. 12-13, convex lens 136 is situated above upper surface 38 of base 36. A collimated ultraviolet light is condensed to the upper surface 38 of base 36 through the convex lens 136. It can be appreciated that film 26 blocks a first portion of the ultraviolet light directed at upper surface 38 of base 36. However a second portion of the ultraviolet light passes through wells 42 in base 36 such that resin 124 in the pathway of the converging exposure beam is photopolymerized with a conic structure pointing to the photodetector in array 102. As heretofore described with respect to the compound eye 10, after curing, the exposed portions of resin 124 serve as waveguides 134a-134g which are self aligned to corresponding ommatidium and photodetectors.

Compound eye 100 further includes a generally arcuate-shaped oil container 140 having an inner surface 142 and an outer surface 144, FIG. 13. Flange 146 projects radially outward from the outer periphery of oil container 140. It is contemplated to fabricate oil container 140 from PDMS or other suitable material. The upper ends of first and second clamping bars and 118 and 120, respectively, extend through flange 146. Clamping elements 148 are positioned on upper ends of clamping rods 118 and 120 so as to capture flange 146 of oil container 140 between clamping elements 122 and clamping elements 148 thereby providing a fluid-tight seal. As best seen in FIG. 13, once assembled, inner surface 142 of oil container 140 and film 26 define oil receiving chamber 150 therebetween.

In order to form the liquid microlenses of the compound eye of the present invention, water droplets 152 are loaded into wells 42 of base 36 through filling hole 154 in oil container 140. Thereafter, oil receiving chamber 150 of oil container 140 is filled with a suitable oil 156, e.g., mineral oil, and filling hole 154 is sealed in any suitable matter, such as by one of the clamping elements 148. The intersection of the hydrophobic film 26 and the hydrophilic reduced diameter portion 50 of wells 42 define contact lines that pin water droplets 152 at the upper edges of apertures 48 so as to form a plurality of liquid menisci 158 at the water-oil interfaces. As heretofore described, when hydrogel microposts 52 are exposed to a predetermined stimulus, e.g., temperature, light, etc., microposts 52 expand and shrink by absorbing and releasing water via the hydrogel network interstitials. This, in turn, results in a volume change in the water received in wells 42. The net physical volume changes in both hydrogel microposts 52 and the water received in wells 42 cause changes in the pressure differences across the water-oil interface (P) which, in turn, directly determines the outcome of the liquid menisci 158, as heretofore described.

As heretofore described, it is contemplated to fabricate hydrogel microposts 52 from a NIPAAm hydrogel that expands at low temperatures and contracts at high temperatures with a volume transition temperature of approximately 50° C. It is noted, however, that this temperature may be tuned for various applications and for the various environments in which compound eye 100 is used. The temperature of the hydrogel microposts 52 may be controlled by microheaters 53. Here, the expansion and contraction of hydrogel microposts 52 only occurs within wells 42 due to the physical restraint of sidewalls 46 of wells 42. At low temperatures, liquid menisci 158 grow because the added physical volumes of hydrogel microposts 52 are larger than the volumes of the water in wells 42 lost to absorption by hydrogel microposts 52. At high temperatures, liquid menisci 158 retreat because the water released from physical shrinking of hydrogel microposts 52 is unable to compensate for the decrease in physical volumes of hydrogel microposts 52. More specifically, as the temperatures increase, the microlenses become more convergent. As a result, the focal lengths of the microlenses are tuned from infinity to several millimetres, thus allowing the microlenses to zoom in on a target area.

Alternatively, the liquid microlenses may be responsive, either entirely or partially, to light. More specifically, hydrogel microposts 52 may be fabricated from a light-responsive hydrogel that responds to the wavelength of the light incident onto them and contract accordingly, pulling down the oil-water interface towards the water and eventually into the water, rendering a more convergent lens. When light is off, the hydrogel microposts 52 expand back, pushing the oil-water interface back towards the oil, thus restoring a more divergent lens. Once again, to pin the oil-water interfaces at the edges of the apertures 48 of wells 42, reduced diameter portions 50 of wells are treated to be hydrophilic and film 26 on upper surface 38 of base 36 is treated to be hydrophobic. Therefore, hydrophobic-hydrophilic contact lines are formed and will pin the oil-water interfaces via surface tension. In this embodiment, the volume of hydrogel microposts 52 is defined through ultraviolet (UV) exposure.

The aforementioned liquid microlenses can smartly focus on objects at different distances. By causing the hydrogel microposts 52 to change their volumes, the microlenses autonomously tune to focus on desired targets. Due to the a hydrogel's ability to convert chemical energy to mechanical energy, the hydrogel microposts 52 simultaneously exhibits both sensing and actuating functions in response to local environments.

It is contemplated to incorporate a compound eye in accordance with the present invention into a variety of instruments. By way of example, a compound eye may be incorporated into a fiber endoscope or a laparoscope 160. More specifically, in order to form laparoscope 160, compound eye 100 is mounted at tip 162 of cable 164. Cable 164 is operatively connected to image acquisition device 165 and controller 167 of image processing and control system, generally designated by the reference numeral 166. Image acquisition device 165 receives images from microlenses of compound eye 100 and performs the necessary image processing to display the images on monitor 170. Image processing and control system 166 further includes central processing unit 172 operatively connected to image processing and control system 166, controller 167 and one or more input devices such as keypad 174. It is intended for keypad 174 to allow a surgeon to input a desired command, e.g., to control the zoom-in/out functions of compound eye 100. The command is processed by central processing unit 172 and provided to controller 167. In response to such command, controller 167 controls the microheaters for the liquid microlenses (ommatidia) of compound eye 100, as heretofore described. As a result, compound eye 100 may be used to zoon in/out of a specific visual area in accordance with the surgeon's commands. As described, laparoscope 160 couples high performance in a compact design. It can be appreciated that laparoscope 160 provides imaging of a desired area without the need for complicated mechanical and electronic systems.

Various modes of carrying out the invention are contemplated as being within the scope of the following claims particularly pointing out and distinctly claiming the subject matter, which is regarded as the invention.

We claim:

1. An artificial compound eye, comprising:
    a microfluidic device defining a plurality of wells therein;
    a plurality of lenses disposed in corresponding wells of the microfluidic device, each lens having a tunable focal length;
    a tuning structure for tuning the focal length of each lens in response to a predetermined stimulus, the tuning structure including a plurality of hydrogels engageable with corresponding lenses, each hydrogel movable between a first configuration wherein the corresponding lens has a first focal length and a second configuration wherein the corresponding lens has a second focal length in response to the predetermined stimulus;
    a plurality of photodetectors, each photodetector detecting an image received by a corresponding lens; and
    a plurality of waveguides, each waveguide guiding the image from a corresponding lens to a corresponding photodetector.

2. The compound eye of claim 1 wherein the predetermined stimulus is temperature.

3. The compound eye of claim 1 wherein microfluidic device includes a slip having a plurality of apertures therethrough, each aperture communicating with a corresponding well.

4. The compound eye of claim 1 wherein each lens includes first and second layers having an interface.

5. The compound eye of claim 4 wherein the first layer is formed from an oil-based fluid and the second layer is formed from a water-based fluid.

6. The compound eye of claim 5 wherein at least of a portion of the second layer of each lens is received in a corresponding well.

7. The compound eye of claim 1 wherein microfluidic device includes a base having a first side and second side, the first side of the base including the plurality of wells formed therein.

8. The compound eye of claim 1 wherein microfluidic device includes a base having a first side and second side, the first side of the base being generally arcuate.

9. The compound eye of claim 1 wherein the microfluidic device includes a base having a first side, a second side and a cover overlapping the first side of the base.

10. The compound eye of claim 1 wherein the microfluidic device includes a base having a first side, a second side and a heating element adjacent the second side of the base.

11. A compound eye, comprising:
    a microfluidic device including a base having an outer surface defining a plurality of wells and an inner surface;
    a first fluid disposed in the plurality of wells;
    a second fluid intersecting the first fluid at a plurality of interfaces, each interface defining a lens having a focal length;
    a tuning structure for tuning the focal length of each lens in response to a predetermined stimulus, the tuning structure includes a plurality of hydrogels positioned in corresponding wells, each hydrogel movable between a first configuration wherein, the corresponding lens has a first focal length and a second configuration wherein the corresponding lens has a second focal length in response to a predetermined stimulus;
    a plurality of photodetectors, each photodetector detecting an image received by a corresponding lens; and
    a plurality of waveguides, each waveguide guiding the image from a corresponding lens to a corresponding photodetector.

12. The compound eye of claim 11 wherein microfluidic device includes a slip having a plurality of apertures therethrough, each aperture communicating with a corresponding well.

13. The compound eye of claim 11 wherein the first fluid is a water-based fluid and the second fluid is an oil-based fluid.

14. The compound eye of claim 11 wherein the outer surface of the base is generally arcuate.

15. The compound eye of claim 11 wherein the microfluidic device includes a cover overlapping the outer surface of the base.

16. The compound eye of claim 11 wherein the microfluidic device includes a heating element adjacent the inner surface of the base.

* * * * *